United States Patent [19]

Courty et al.

[11] Patent Number: 4,596,782

[45] Date of Patent: Jun. 24, 1986

[54] PROCESS FOR MANUFACTURING CATALYSTS CONTAINING COPPER, ZINC AND ALUMINUM, USEFUL FOR PRODUCING METHANOL FROM SYNTHESIS GAS

[75] Inventors: Philippe Courty, Houilles; Christine Travers; Daniel Durand, both of Rueil-Malmaison; Alain Forestière, Vernaison; Patrick Chaumette, Rueil-Malmaison, all of France

[73] Assignee: Institut Francais du Petrole, Rueil-Malmaison, France

[21] Appl. No.: 695,021

[22] Filed: Jan. 25, 1985

[30] Foreign Application Priority Data

Jan. 27, 1984 [FR] France ............................ 84 01256

[51] Int. Cl.$^4$ .................. B01J 21/04; B01J 23/06; B01J 23/72
[52] U.S. Cl. .................. 502/302; 502/303; 502/304; 502/329; 502/342
[58] Field of Search ............ 502/303, 342, 329, 302, 502/304; 518/713

[56] References Cited

U.S. PATENT DOCUMENTS

| | | | |
|---|---|---|---|
| 3,388,972 | 6/1968 | Reitmeier et al. | 502/342 X |
| 3,709,919 | 1/1973 | Magoon | 502/342 X |
| 4,111,847 | 9/1978 | Stiles | 502/342 |
| 4,257,920 | 3/1981 | Sugier et al. | 502/302 |
| 4,483,943 | 11/1984 | Windawi et al. | 502/342 |

FOREIGN PATENT DOCUMENTS 3005551  8/1981  Fed. Rep. of Germany ...... 502/342

Primary Examiner—W. J. Shine
Attorney, Agent, or Firm—Millen & White

[57] ABSTRACT

Manufacture of catalysts containing at least three essential metals consisting of copper, zinc and aluminum.

The process for manufacturing the catalyst comprises the formation of homogeneous amorphous precipitate of the above-mentioned metals, followed with a washing in two steps, first with water, then with an acid solution.

These catalysts are used in balanced reactions involving alcohols and synthesis gas, particularly in methanol synthesis.

22 Claims, No Drawings

PROCESS FOR MANUFACTURING CATALYSTS CONTAINING COPPER, ZINC AND ALUMINUM, USEFUL FOR PRODUCING METHANOL FROM SYNTHESIS GAS

This invention concerns a process for manufacturing a catalyst, of essentially homogeneous composition, highly active, stable and selective, useful in processes involving a balanced reaction of carbon oxides (CO, $CO_2$) with hydrogen, particularly for producing methanol from synthesis gas and in reactions of decomposing primary alcohols and particularly methanol or ethanol to a mixture containing carbon oxides and hydrogen.

These catalysts comprise at least three metals: copper, aluminum and zinc; they optionally further contain at least one metal from the group of rare earths, having atom numbers from 57 to 71 included and/or zirconium; they may also contain, in addition, 0.01–1% of at least one metal selected from the group consisting of palladium, rhenium and platinum and/or 0.5–5% of silver.

The catalysts with a base of copper and zinc oxides are known since many years; they have been disclosed as soon as 1933 by DODGE (U.S. Pat. No. 1,908,696). In the U.S. Pat. Nos. 3,388,972, 3,546,140 and 3,790,505, the American Company C.C.I. discloses the use of ternary compositions Cu-Zn-Al for the conversion at low temperature of carbon monoxide (CO), and for the synthesis of methanol. In the French Pat. No. 2,133,467 the SHELL Company recommends the use of Cu-Zn-Dy catalysts for the synthesis of methanol; Dy or didymium being the mixture of at least two oxides of rare earth metals having atomic numbers from 57 to 71 included. This Company shows that the best results are obtained with catalysts containing several oxides of rare earth metals; the use of aluminum is not suggested.

Various methods for preparing Cu-Zn-Al catalysts are disclosed, particularly in the U.S. Pat. No. 3,923,694 (I.C.I.) and U.S. Pat. No. 4,279,781 (United catalysts).

The addition of precious metals, as chlorides, has been claimed, in particular in the U.S. Pat. No. 4,257,920 which relates to Cu-Al-Zn catalysts prepared by admixing oxides and/or carbonates of said metals, in the presence of an aluminous cement, the catalyst further containing at least one oxide of rare earth metals of atomic numbers from 57 to 71 included.

It may be observed that the prior art does not suggest processes wherein the obtained catalyst is essentially homogeneous, particularly in the distribution of metals Cu-Zn-Al. For example, U.S. Pat. No. 3,923,694 disclosed a sequential co-precipitation where a spinel precursor containing aluminum and zinc is first obtained, and then a binary Cu-Zn compound is co-precipitated on this precursor. Many patents, for example U.S. Pat. Nos. 3,388,972, 3,546,140, and French Pat. No. 2,027,162, disclose processes wherein aluminum, as essential component of the catalyst is introduced therein as oxide or as hydroxide (U.S. Pat. No. 4,279,781).

A catalyst for methanol synthesis, when activated and ready for use, must have a concentration of alkali metals as low as possible. Alkali metals are generally introduced during co-precipitation; contents lower than 0.1% and preferentially lower than 0.05% are recommended (U.S. Pat. No. 3,923,694).

Although the process of hot precipitation in the presence of diluted solutions, as disclosed in the prior art and, for example, in the above-mentioned patent, results in the effective formation of hydrated precursors, at least partially crystallized, which may be easily dealkalinized by washing, these precursors, while containing divided phases, are not homogeneous, i.e., they do not have an identical composition at any point thereof, at a scale of 1–5 nanometers. The hydrated precursor, at least partially crystallized, is a mixture of at least three phases; a ternary phase Cu-Al-Zn, with $$\frac{Cu + Zn}{Al} = 3 \text{ (atoms. atom}^{-1}),$$

of the hydrotalcite type; a binary phase of mixed copper and zinc hydroxycarbonate, rosacite, a copper hydroxycarbonate, malachite; as well as, optionally, other phases, such as, for example, spinel $Zn\,Al_2O_4$, disclosed in U.S. Pat. No. 3,923,694. The heterogeneous composition of these catalysts results in relatively low activity, selectivity and stability, even when they initially contain an at least partly well dispersed copper oxide. A detailed description of the simultaneous formation of these phases is given in various papers, for example in F. TRIFIRO et al, Preparation of Catalysts III p. 723–733- (1983) Elsevier Science Publishers (Amsterdam).

For obtaining a homogeneous hydrated precursor, it is necessary to proceed by co-precipitation in such conditions that the rate of growth of microcrystals is much more rapid than the rate of formation of microcrystalline nuclei. The resulting structure is thus disordered, without particular crystalline organization, but very homogeneous. The specific conditions for Cu-Al-Zn, with the optional addition of at least one metal Ln of the group of rare earths, of atomic numbers from 57 to 71 included, and/or of zirconium and/or silver and/or palladium, are explained hereinafter.

But, as above mentioned, the catalysts for the synthesis of methanol, in order to give good performances, must also contain the lowest possible proportion of alkali metals.

The catalysts prepared from amorphous hydrated precursors contain a too high amount of sodium, directly proportional to the concentration of the initial solutions, corresponding to about 0.1–0.2% by weight of sodium with respect to the total weight of metals.

Now, it has been discovered surprisingly that it was possible to remove the alkali metals without changing the homogeneity of the catalyst, by a very specific procedure which forms one of the objects of the invention: the wet precipitate is dried, thermally activated, finely crushed, contacted with an excess of acid aqueous solution (pH lower than 6.7), settled, suspended in water, dried, for example by spray-drying, then, if necessary, shaped by any known process. The resultant catalyst is particularly active, selective and stable.

The catalysts according to the invention advantageously contain the above-mentioned metals in the following proportions, expressed in percent of the total metal weight:

| | |
|---|---|
| copper | 25–80%, preferentially 45–70% |
| zinc | 10–50%, preferentially 15–35% |
| aluminum | 4–25%, preferentially 4–20% |
| rare earth metals and/or zirconium | up to 20%, preferentially 2–18%. |

They may optionally contain, in addition, up to 1% by weight for example, and preferentially 0.01–0.9% by weight, of at least one metal selected from the group consisting of Pd, Re, Pt and/or up to 5% by weight for example, and preferably 0.5-5%, of silver metal.

The homogeneity of composition of the catalysts on the scale of a nanometer may be controlled for example by X-ray spectrometry in a scanning transmission electronic microscope (STEM) equipped with an X-ray detector of the doped silicium type, covering the required space zone (e.g. 1-20 keV for compositions claimed in this invention). The operation is as follows: a representative sample of the catalyst is crushed to fine powder (for example with a particle size smaller than 10 μm), then deposited on an electronic microscope grid, optionally after suspension in an organic solvent, subsequently evaporated. The electronic microscope grid is made of a material which must be so selected as to avoid spectral interferences or parasitic signals (for this reason copper grids cannot be used).

The best results can be obtained with such materials as nylon, beryllium, carbon.

The microscope must simultaneously give images with high resolution (0.5-1 nm) in scanning mode (STEM mode) and have a high sensitivity in the mode of X-ray micro-analysis. A trade apparatus such as STEM Vacuum Generator HB 501 is quite convenient (limit sensitivity better than 1,000 atoms of a given element) to determine the scale of homogeneity of the catalyst.

After selection of the zone to be analyzed (typically 2-5 nm), several numberings over a period of 100-1,000 s, are simultaneously performed, so as to obtain a numbering statistic of sufficient accuracy (better than 10%).

From the measured intensities of the various selected peaks for the various elements contained in the sample, it is possible to determine their relative concentrations and then their respective atomic ratios, according to techniques well known in the field of X-ray transmission (see for example REED S. J. B. Electron microprobe Analysis, Cambridge University Press 1975), for each of the particules forming the sample.

The compared samples must all have the same thickness. The average values of the correction coefficient are the following:

Correction coefficients (on the basis of $Cu-K_\alpha=1$).

| Measurement on the line | Element | Coefficient |
| --- | --- | --- |
| $K_\alpha$ | Copper | 1 |
| $K_\alpha$ | aluminum | 4.86 |
| $K_\beta$ | zinc | 4.68 |

These coefficients have been determined by the applicant from mixed oxides roasted at high temperature.

$CuAl_2O_4$, $ZnAl_2O_4$, $Cu_{1-x}Zn_xAl_2O_4$ (x=0.25—0.50—0.75) constituting the reference samples.

The atomic ratio Zn/Cu will be calculated for example as follows ($i_{k\beta}$Zn and $i_{k\alpha}$Cu are the uncorrected average intensities over several numberings).

Zn/Cu = 4.68 $i_{k\beta}$ Zn/$iK_\alpha$ Cu.

The best results, in terms of activity, selectivity and stability, are obtained with catalysts having atomic ratios Cu/Zn and Cu/Al varying by less than about 15% and preferentially less than about 10% from the average value of said ratio, at the scale of 50 Å (5 nanometers).

In order to obtain homogeneous catalysts, it is essential to first prepare a solution (homogenous by definition) containing copper, zinc and aluminum, together with optionally at least one element from the rare earths and/or zirconium and/or optionally silver and/or palladium, then to convert this solution by co-precipitation to a solid substance, called catalyst precursor, always of highly homogeneous composition.

Cu, Zn, Al metals, with optionally rare earths and/or zirconium and/or silver and/or palladium, are used as soluble compounds, preferably soluble in acid medium, although the amino complexes (soluble in ammonia) of copper, zinc and palladium may be optionally added to the co-precipitation alkaline reactant.

Soluble oxides (for example $Re_2O_7$), hydroxides, carbonates, hydroxycarbonates soluble in acid medium (e.g. Cu $CO_3$-Cu $(OH)_2$, $ZnCO_3$, Zn $(OH)_2$), nitrates, oxalates, tartrates, citrates, acetates, acetylacetonates or even anionic combinations such as aluminate or perrhenate, will be used for example. The soluble salts used most frequently are the nitrates.

For manufacturing these catalyst masses, it is essential to prepare them according to such techniques as to obtain a product as homogeneous as possible and to avoid segregation of the different elements during the different unitary manufacturing steps.

One procedure consists of preparing, by at least one co-precipitation reaction step (a), a hydrated homogeneous precursor containing Cu, Zn, Al metals and optionally at least one metal from the rare earths and/or zirconium and/or silver and/or palladium. The co-precipitation reaction is conducted by mixing together, under hereinafter defined operating conditions, a solution of soluble salts of Zn, Cu, Al metals, optionally rare earths and/or zirconium and/or silver and/or palladium and a solution of sodium and/or potassium carbonate and/or hydrogeno-carbonate and/or hydroxide, so as to obtain a co-precipitate which, after subsequent washing step (b), forms the homogeneous hydrated precursor, containing said metals at least partly as hydroxycarbonates. By "hydrogeno-carbonate" is meant the hydrogen carbonates, usually termed "bicarbonates."

All the techniques and apparatuses described in the prior art may be used or applied for carrying out the invention. For example, the solution of salts of Cu, Zn, Al and other metals may be added to the alkaline solution or inversely. Preferably, both solutions will be added simultaneously and their flow rates adjusted in relation with the pH measured in the reaction zone, in a reactor comprising an efficient stirring system. Preferably both solutions are contacted in a zone of maximum turbulence defined by the volume surrounding the stirring apparatus, inside the reaction volume.

The operation is preferably continuous, the average residence time, expressed in minutes and defined as the ratio of the total volume flow rate (liters/minute) of the solutions introduced into the reactor to the volume of said reactor, expressed in liters, may for example vary from about 0.1 to 30 minutes, preferably about 5-12 minutes. The useful volume of the reactor may vary from a few liters to about 100 liters and the reaction product is recovered continuously, then fed for example to a press filter or to a rotary filter, where it is washed.

A preferred embodiment of the invention consists of reacting a solution of salts of Cu, Zn, Al metals, together with, optionally, at least one soluble salt of at least one metal Ln, wherein Ln designates at least one metal from the rare earths having an atomic number from 57 to 71 included or zirconium and/or palladium and/or silver, heated to a temperature of about 20°-80° C. and containing about 0.2-0.6 gram-atoms of all the metals (Cu+Al+Zn+Ln+Pd+Ag) per liter, with a solution of sodium and/or potassium carbonate and/or hydrogenocarbonate and/or hydroxide containing about 0.4–1.2 gram-atoms of alkali cations per liter, at a temperature of about 20°–80° C., the co-precipitation reaction step (a) being conducted at about 20°–80° C., the pH measured in the reaction volume being set at a value ranging from about 6.3 to 7.3 pH units and the residence time of the mixture (co-precipitate + mother liquors) in the reaction volume being not more than about 12 minutes. When the cation is sodium, the solution may further contain, optionally, rhenium, as perrhenate anion ($ReO^-_4$).

The resultant homogeneous hydrated precursor is amorphous in X-ray diffraction, giving by X-ray diffraction and goniometrical recording a "flat" diagram. This product is then washed step (b) so as to reduce its content of alkali metals (expressed by weight with respect to the total weight of the metals) to about 0.1–0.3% by weight, preferably about 0.05–0.2% by weight.

Step (c) of the catalyst manufacture consists of a drying and a thermal activation or calcination as described below.

Drying of the mixed homogenized co-precipitate may be achieved by any known process; for example by spray-drying. A homogeneous product is obtained, as calibrated powder containing about 60–80% by weight of potential oxides. The product may also be dried in a stove, for example at about 50°–150° C., under air scavenging, so as to bring, if necessary, its potential oxides content to about 60–80% by weight. It is recommended to avoid the stagnation of the precipitate in the presence of steam partial pressures close to the saturating vapor pressure at the considered drying temperature. Such treatments may result in a partial dehydration of the precipitate with a crystallization of cupric oxide to big crystallites.

The thermal activation consists of treating the dried precipitate at a temperature of about 250°–500° C., preferably about 300°–380° C., for a sufficient time, e.g. at least 0.5 hour, to obtain a homogeneous activated catalyst containing no more than 12% by weight of volatile matters (the proportion of volatile matters is measured for example by activating, in the presence of air, a given weight of product, placed in a boat and calcined at 500°–600° C. for 4 hours).

The thermal activation may be conducted for example in the presence of an inert gas of 0–50% oxygen content.

The drying and thermal activation may also be combined by using the techniques of flash-roasting or spray-calcination, the product being then pulverized in a stream of combustion gas.

The mixture of thermally activated oxides obtained in step (c) is then optionally crushed so as to obtain a product of particle size smaller than about 0.5 mm and preferably smaller than 0.05 mm. This crushing step (d) is only performed when the mixture of oxides obtained in step (c) has a particle size greater than 0.5 mm.

The crushed product or the mixture of oxides obtained in step (c), of particle size smaller than about 0.5 mm and preferably smaller than about 0.05 mm, is then more completely dealkalinized step (f) by washing according to the following procedure: An aqueous suspension step (e) containing about 0.5–10% by weight of oxides from the mixture of oxides of particle size smaller than about 0.5 mm, as above obtained, and preferably containing about 1.5–6% by weight of said mixture of oxides, is formed. Dealkalinization is performed by vigorous stirring of said suspension for a sufficient time to dissolve sodium and potassium into the solution; the temperature of the solution is advantageously about 15°–45° C. The washing time varies from about 0.2 to 1 hour. The washing may be performed continuously on a band filter, or still by percolation, preferably by using as washing liquid a diluted aqueous solution of acid, preferably nitric acid, having a pH lower than about 6.7, preferably lower than about 6 and advantageously ranging from about 2 to 5. During the washing step, the pH increases and may reach values higher than about 7, as a result of the dealkanization of the solid.

The crushing and acid washing of the oxide suspension may also be combined in a single unitary operation, for example by wet crushing in the presence of at least a portion of the diluted acid solution.

The kinetics of dealkalinization has been determined by successive titrations of alkali content of the washing solution; a standard time of about 30 minutes is generally sufficient to bring the alkali content, expressed as weight of alkali in proportion to the total weight of the metals, below 0.05% and, for example, preferably to about 0.005–0.035%.

The dealkalinized catalyst, separated from the washing waters by filtration step (g) is then dried step (h), preferably in the following operating conditions:

The drying rate is such that the residence time of the solid within the heat range 60°–150° C. be no longer than about 10 seconds and preferably about 5 seconds. The residence time is advantageously 1–10 seconds and preferably 1–5 seconds. A preferred procedure consists of adding to the precipitate a minimum amount of water and to subject it to spray-drying. A homogeneous product is obtained which contains about 60–80% by weight of oxides and 40–20% by weight of water. Any other procedure complying with this requirement may also be used. An apparatus, for example of the rotary type, for drying while stirring, can also be used. As a result of the rotation speed, a thin layer of product is formed, which is instantaneously dried. The residence time in the apparatus is about 10 seconds. Residence times longer than 10 seconds result in a decrease of the catalyst activity by recrystallization of copper.

The catalyst, thermally activated step (i) at a temperature of about 250°–500° C., may then optionally be contacted with an aqueous or organic solution of at least one metal selected from the group consisting of palladium, platinum, rhenium and/or silver, so as to substantially uniformly disperse said metal and to obtain, after redrying and thermal reactivation as above stated, a catalyst wherein said metal is well dispersed (the dispersion may be measured for example by chimisorption of the reacting gases CO, $H_2$, on said metal). With the exception of halides and sulfates, all the soluble salts, e.g. nitrates, acetylacetonates, as well as complexes, for example nitrosamminated, amminated or carbonylated complexes, can be used.

The shaping of the catalyst may be achieved by any known process, for example by treatment of the wet precipitate (after deposition of additional metals), of the dried precipitate, of the thermally activated precipitate; for the shaping operation, extrusion, bowl granulation, oil-drop, can be used. The thermally activated homogeneous product may optionally be compacted, crushed, for example to particles of less than 0.5 mm, admixed in a proportion of 0.5–5% of its weight with a pelletizing adjuvant selected from the group consisting of graphite, stearic acid, stearates and, optionally, a porosity adjuvant selected from cellulose and cellulose-containing powders of vegetable origin, ammonium carbonates, combustible textile fibers and naphthalene. Finally, the product may be pelletized to solid cylinders of 2-6 mm diameter or toric cylinders of 3-6 mm external diameter and 1-4 mm internal diameter and of 2-6 mm height.

The catalysts shaped to pellets will be optionally subjected to a final thermal activation in the above-mentioned operating conditions.

The thermally activated catalyst, ready for use, consists of a very homogeneous association of oxides. In this very homogeneous association of oxides, the metals, particularly copper, zinc and aluminum, are distributed very homogeneously, at a scale of 5 nm and the relative variations of the atomic ratios Cu/Al,Cu/Zn are smaller than about 15% and, preferentially less than about 10%. The specific surface of said catalysts varies from 50 to about 150 $m^2 g^{-1}$.

The conditions of use of said catalysts for manufacturing methanol are usually as follows: the catalyst charge, in the reactor, is first prereduced by a mixture of inert gas (e.g. nitrogen) with at least one reducing compound selected from the group consisting of hydrogen, carbon monoxide, alcohols, $C_1$ and $C_2$ aldehydes, the molar ratio "reducing compound/reducing compound+inert gas" being from 0.001:1 to 1:1.

The reduction temperature generally varies from about 100° to 300° C. but preferably from about 140° to 260° C., the total pressure is usually about 0.1–10 MPa and preferably about 0.1–6 MPa; the hourly volume velocity is usually from $10^2$ to $4.10^4$ hour$^{-1}$ and preferably from $5.10^2$ to $10^4$ hour$^{-1}$ (under normal temperature and pressure (NTP)).

The reduction is first conducted, for example, at about 140°–160° C. in the presence of the above-mentioned reducing mixture and with a molar ratio "reducing gas/reducing gas+inert gas" ranging from about 0.001 to 0.1 and preferentially from about 0.005 to 0.05, for a sufficient time to obtain the same concentrations of reducing gas at the inlet and at the outlet of the reactor (thus making obvious that the first reduction step is completed). It may also be advantageous, in a second step, to increase the temperature and, optionally, the concentration of reducing gas, and to continue the reduction under more severe thermal conditions.

The reduction temperature then varies between about 160° and about 240° C., the molar ratio "reducing gas/reducing gas+inert gas" is then about 0.01–1, and preferentially 0.05–1, the pressure and hourly volume velocity remaining within the above-mentioned ranges.

The prereduction of the catalyst will be preferentially conducted in liquid phase when, subsequently, the methanol synthesis reaction is performed in liquid phase.

The methanol synthesis reaction itself is conducted in the following operating conditions: the pressure is usually about 2–15 Mpa, preferably about 4–15 MPa, the molar ratio "$H_2/2 CO+3CO_2$" is advantageously about 0.4–10 but preferably 0.5–4, when the reaction is conducted in gaseous phase, and preferably about 0.5–1.5 when the reaction is conducted in liquid phase. The temperature ranges from about 200° to 300° C., preferably from about 220° to 270° C.

The hourly volume velocity (expressed in volume NTP of gas mixture per volume of catalyst and per hour) is usually from about 1,500 to 60,000 h$^{-1}$ and preferably from 2,000 to 20,000 h$^{-1}$.

The catalyst may be used as fine calibrated powder (about 10–700 μm) or as particles of about 2–10 mm diameter, in the presence of a gas phase or of a liquid (in the operating conditions) phase and a gas phase. The liquid phase may consist of one or more hydrocarbons having at least 5 and preferably at least 10 carbon atoms.

In this embodiment, it is preferable that the surface velocities of the gas and liquid, under the temperature and pressure conditions of the process, be at least about 1.5 cm/sec. and preferably at least about 3 cm/sec.

By surface velocity, it is intended to mean the ratio of the flow rate by volume to the cross-sectional area of the reactor, when empty of catalyst.

The conditions of use of said catalysts for decomposing $C_1$ to $C_5$ primary alcohols and particularly methanol and ethanol are usually as follows: the catalyst charge, in the reactor, is first prereduced by a mixture of inert gas (e.g. nitrogen) and at least one reducing compound selected from the group consisting of hydrogen, carbon monoxide, $C_1$ and $C_2$ alcohols and aldehydes, the molar ratio: "reducing compound/reducing compound+inert gas" being from 0.001:1 to 1:1.

The reduction temperature generally ranges from about 100° to 300° C. but preferably from about 140° to 260° C.; the total pressure is usually from about 0.1 to 10 MPa and preferably from about 0.1 to 6 MPa; the hourly volume velocity is usually from $10^2$ and $4.10^4$ hour$^{-1}$ and preferably from $5.10^2$ to $10^4$ hour$^{-1}$ (Normal temperature and Pressure (NTP)).

The reduction is first conducted, for example at about 140°–160° C., in the presence of the above-mentioned reducing mixture and with a molar ratio "reducing gas/reducing gas+inert gas" ranging from about 0.001 to 0.1 and preferentially from about 0.005 to 0.05, for a sufficient time to obtain the same concentrations of reducing gas at the inlet and the outlet of the reactor (thus making obvious that the first reducing step is completed). It may be advantageous in a second step to increase the temperature and optionally the concentration of reducing gas and to continue the reduction under more severe thermal conditions.

The reduction temperature then varies from about 160° to about 240° C. The molar ratio "reducing gas/reducing gas+inert gas" is then from 0.01 to 1, preferentially from 0.05 to 1, the pressure and hourly volume velocity being within said above-mentioned ranges.

The decomposition reaction itself is conducted in the following operating conditions: the pressure is usually about 1–6 MPa, preferably about 2–5 MPa. The temperature is about 200°–320° C., preferably about 220°–300° C.

The hourly volume velocity of the charge (expressed in liters of charge per liter of catalyst and per hour) is usually about 0.1–5 h$^{-1}$ and preferably about 0.5–3 h$^{-1}$.

The following examples describe various embodiments of the invention without limiting the scope thereof.

EXAMPLE 1 (Catalyst A)

241.6 g of trihydrated cupric nitrate (1 g at Cu), 150 g of nonahydrated aluminum nitrate (0.4 g at Al), 89.2 g of hexahydrated Zinc nitrate (0.3 g at Zn) are dissolved in 3 liters of bi-exchanged water in order to obtain a solution (solution I) containing 0.57 g at of metals per liter.

Separately, 243,3 g of disodic carbonate are dissolved into 4 liters of water. The resultant solution II contains 1.15 g at of sodium per liter.

The reaction is conducted in a reactor of 1,100 ml capacity operating continuously. Both solutions I and II are simultaneously introduced into the reactor, previously fed with one liter of water at a temperature of 60°–70° C. The temperature is maintained at 60°–70° C. during the precipitation. The residence time is about 10 mn.

The flow rates are adjusted in relation with the pH which varies from 6.8 to 7.2 during the whole reaction time. The reaction product is continuously recovered in another reactor, filtered and washed three times with 12 liters of bi-exchanged water. The resulting product then contains 25% by weight of potential oxides, in proportion to its total weight. The precipitate is then dried in a ventilated stove, in open circuit, at 40° C. for 16 hours, then at 90° C. for 3 hours. The resultant dry product then contains 80% by weight of potential oxides in proportion to its total weight and has a flat diagram in X-ray diffraction which characterizes an amorphous compound. The microscopic survey reveals a good homogeneity of the product. The product is then thermally activated for 3 hours at 350° C. in air. The volatile matter content is then 10% by weight.

The resultant product, containing 0.17% by weight of sodium, is then crushed to a particle size of about 0.1 mm and then dealkalinized as follows: 120 g of oxides are suspended in 2.5 liters of bi-exchanged water, acidified with $HNO_3$ to a pH of 4.5 and vigorously stirred for one hour to favour sodium dissolution. The product is then separated from the washing waters by filtration, suspended again in about 250 cc of water and spray-dried at 120° C. for 5 seconds. The sodium content, expressed in percent by weight of metal in proportion to the total weight of the metals of the catalyst, is then 0.020%. This dried catalyst is roasted for 3 hours at 350° C. and then pelletized to solid cylinders of 4 mm diameter, after addition of 2% by weight of graphite. Before being charged into the unit, catalyst A is thermally activated a last time for 2 hours at 350° C. The content of volatile matters is then 3% by weight with respect to the catalyst weight.

The developed specific surface is about 70 $m^2 \times g^{-1}$. The microscopic survey shows a good homogeneity of the product.

The Cu/Zn atomic ratio varies to a very small extent and ranges from 3.05 to 3.6 within the whole solid volume. The maximum variation of the Cu/Zn ratio is about 10% of its average value.

The Cu/Al atomic ratio varies from 2.3 to 2.7 in the whole solid volume. The maximum variation of the Cu/Al ratio is about 9% of its average value.

EXAMPLE 2 (comparison-catalyst A 1)

The preparation of catalyst A1 is performed according to the method of example 1, except that the drying, after dealkalinization, is conducted in a ventilated stove, with open circuit, for 16 hours at 40° C., then 3 hours at 120° C. The analysis by X-ray diffraction of the resultant product shows a substantial heterogeneity in relation with the partial crystallization of copper oxide during the drying step. The subsequent steps, roasting and pelletizing, are the same as in example 1.

EXAMPLE 3 (comparison-catalyst A 2)

The preparation of catalyst A 2 is conducted according to the same method as in example 1, except for dealkalinization which is conducted in basic medium: the precipitate is suspended again in 2 liters of bi-exchanged water containing 2 g of ammonium bicarbonate. The pH of the resultant washing solution is 8.5. After separation of the washing waters by filtration, the precipitate is again suspended in about 250 cc of bi-exchanged water, then instantaneously spray-dried. The thermal treatments and the pelletizing step are the same as described in example 1.

EXAMPLE 4 (comparison-catalyst A 3)

Catalyst A 3 is prepared according to the procedure described in example 1, without dealkalinization step. The resultant catalyst contains 0.224% by weight of residual sodium in proportion to the total weight of metals.

EXAMPLE 5 (catalyst B)

241.6 g of trihydrated cupric nitrate (1 g. at. Cu), 112.5 g of nonahydrated aluminum nitrate (0.3 g. at. Al), 64.95 g of hexahydrated lanthanum nitrate (0.15 g. at. La), 133.8 g of hexahydrated zinc nitrate (0.45 g. at. Zn) are dissolved into 3.5 liters of water so as to obtain a solution (solution I) containing 0.54 g. at. of metals per liter.

Separately, 272 g of disodic carbonate are dissolved into 4.5 liters of water. A solution II is obtained which contains 1.14 g. at. of sodium per liter. The different preparation steps are the same as those described in example 1. The sodium content by weight of the catalyst is 0.032% of the total weight of metals.

EXAMPLE 6

Catalyst B 1 is prepared according to the procedure described in example 5, except that the precipitate is dealkalinized by two successive acid washings. The sodium content is then 0.010% by weight of sodium in proportion to the total weight of metals.

EXAMPLE 7 (catalyst C)

241.6 g of trihydrated cupric nitrate (1 g. at. Cu), 150 g of nonahydrated aluminum nitrate (0.4 g. at. Al), 22 g of hexahydrated cerium nitrate (0.05 g. at. Ce), 104 g of hexahydrated zinc nitrate (0.35 g. at. Zn) are dissolved into 3.5 liters of bi-exchanged water, so as to obtain a solution I containing 0.51 g. at. of metals per liter.

Separately, 257.6 g of disodic carbonate are dissolved into 4.2 liters of bi-exchanged water. The resultant solution II contains 1.16 g. at. of sodium per liter. The precipitation, washing, dealkalinization, thermal activation and pelletizing steps are identical to those described in example 1. The sodium content by weight of the final catalyst is 0.030% of the total weight of metals.

EXAMPLE 8 (catalyst D)

241.6 g of trihydrated cupric nitrate (1 g. at. Cu), 168.75 g of nonahydrated aluminum nitrate (0.45 g. at. Al), 104 g of hexahydrated zinc nitrate (0.35 g. at. Zn), 1.61 g of palladium nitrate (0.007 g. at. of Pd) are dissolved into 3.5 liters of bi-exchanged water.

The resultant solution I contains 0.52 g. at. of metals per liter.

Separately, 259 g of disodic carbonate are dissolved into 4.2 liters of water so as to obtain solution II containing 1.16 g. at of sodium per liter. The preparation steps are identical to those described in example 1.

The final catalyst contains 0.75% by weight of palladium and 0.02% by weight of sodium, in proportion to the total metals weight.

EXAMPLE 9 (comparison-catalyst E 1)

Solution I, containing salts of Cu, Al, Zn metals in the proportions of the preceding examples, in a total proportion of 0.51 g. at. of metals per liter, is precipitated by a disodic carbonate solution containing 1.16 g. at. of sodium per liter. The product obtained after precipitation is washed, roasted, dealkalinized to a sodium content of 0.020% by weight, in proportion of the total metals weight, spray-dried, according to the methods described in example 1.

The oxide content is then 72%. The product is then roasted for 3 hours at 350° C.

Palladium is deposited by admixing 100 g of roasted product with 150 cc of aqueous solution containing 1.49 g of dihydrated palladium chloride. The Pd metal content is 0.75% by weight with respect to the total metals weight. The thick paste is then suspended again in a minimum amount of water, then spray-dried at 120° C. for 5 seconds. The oxides content is then 70%. The product is roasted for 2 hours at 400° C., then shaped according to the method described in example 1.

EXAMPLE 10 (catalyst E)

Catalyst E differs from catalyst $E_1$, described in example 9, in that palladium is deposited from a solution of palladium acetyl-acetonate Pd $(C_5H_7O_2)_2$. 100 g of roasted precipitate are mixed with 150 cc of ethyl alcohol containing 2.130 g of palladium acetylacetonate. The Pd metal content is 0.75% by weight of the total metals weight. The drying, calcination and shaping are the same as those described in example 9 for catalyst E 1.

EXAMPLE 11 (catalyst F)

193.28 g of trihydrated copper nitrate (0.8 g. at. Cu), 4.25 g of silver nitrate (0.025 g. at. Ag), 131.25 g of nonahydrated aluminum nitrate (0.35 g. at. Al), 148.68 g of dihydrated zinc nitrate (0.5 g. at. Zn) are dissolved into 3.5 liters of water to obtain a solution I containing 0.48 g. at. of metals per liter. Separately, 239.7 g of disodic carbonate are dissolved into 4 liters of bi-exchanged water. The resultant solution II contains 1.13 g at. of sodium per liter. The precipitation, washer, dealkalinization, thermal activation and pelletizing operations are the same as those described in example 1. The residual sodium and silver contents of the catalyst are respectively 0.0196% and 2.82% by weight of metal with respect to the total metals weight.

EXAMPLE 12 (catalyst G)

Solution I, containing Cu, Al, Zn metals salts in the proportions of example 8, in a total proportion of 0.51 g. at. of metals per liter, is precipitated, by a solution of disodic carbonate containing sodium perrhenate (NaReO$_4$) obtained by dissolving 257.6 g of disodic carbonate and 1.172 g of NaReO$_4$ into 4.1 liters of distilled water. The obtained solution II contains 1.18 g. at. of sodium per liter. The product obtained after precipitation is washed, calcined, dealkalinized, spray-dried, activated and shaped according to the methods described in example 1. The residual sodium and rhenium contents of the catalyst are respectively 0.034% and 0.749% by weight with respect to the total metals weight.

EXAMPLE 13 (catalyst H)

241.6 g of trihydrated copper nitrate (1 g. at. Cu), 112.5 g of nonahydrated aluminum nitrate (0.3 g. at. Al), 43.3 g of hexahydrated lanthanum nitrate (0.1 g. at. La), 133.81 g of hexahydrated zinc nitrate (0.45 g. at. Zn) and 2.30 g of palladium nitrate (0.01 g. at. Pd) are dissolved into 3.5 liters of bi-exchanged water. The resultant solution I contains 0.53 g. at. of metals per liter.

266.2 g of disodic carbonate are dissolved separately into 4.2 liters of distilled water. A solution II containing 1.19 g. at. of sodium per liter is thus obtained. The precipitation, washing, dealkalinization, thermal activation and pelletizing operations are the same as those described in example 1. The residual sodium, palladium and lanthanum contents by weight are respectively 0.0256, 0.92 and 11.97% with respect to the total metals weight.

EXAMPLE 14 (catalyst I)

241.6 g of trihydrated cupric nitrate (1 g. at. Cu), 75 g of nonahydrated aluminum nitrate (0.2 g. at. Al), 40 g of tetrahydrated praseodymium nitrate (0.1 g. at. Pr) and 163.55 g of hexahydrated zinc nitrate (0.55 g. at. Zn) are dissolved into 4 liters of bi-exchanged water. The solution I containing 0.46 g. at. of metals per liter is obtained. Separately, 264.7 g of disodic carbonate are dissolved into 4.5 liters of bi-exchanged water, so as to obtain a solution II containing 1.11 g. at. of sodium per liter. The different steps of catalyst manufacture are then the same as described in example 1. The content by weight of residual sodium in proportion to the total weight of metals is 0.032%.

EXAMPLE 15 (catalyst K - comparison)

The manufacture of catalyst K is conducted as in example 1, but without fine crushing of the roasted product. The product obtained after roasting, containing 0.17% by weight of sodium, is very roughly crushed to particles of about 2 mm size. The crushed product is then dealkalinized, filtered, dried and then roasted according to the procedure described in example 1. The sodium content of the final product is 0.07% by weight of metal in proportion to the total metals weight of the catalyst.

EXAMPLE 16 (catalyst L - comparison)

The manufacture of catalyst L is performed according to the method of example 1, except that the drying after dealkalinization is a spray-drying, for a period of 60 seconds at 120° C., of the dealkalinized product. The activation procedure is the same as in example 1.

EXAMPLE 17 (catalyst M - comparison)

The manufacture of catalyst M is performed according to the method of example 1, except that the residence time of the precipitate in the mother liquors of step (a) is about 45 minutes. The resultant product is partially crystallized, as shown by the goniometrical recording of the X-ray diffraction diagram. All the subsequent steps are identical to those described in example 1.

All the catalysts described in examples 1 to 17 are tested for methanol synthesis in gaseous phase.

The catalysts are primarily reduced in situ by a mixture of hydrogen and nitrogen, consisting of nitrogen containing 6% of hydrogen, by successive temperature stages between 160° C. and 240° C., at atmospheric pressure.

The tests conditions are as follows :

| temperature | 220° C.-270° C. |
|---|---|
| pressure | 60 bars |
| hourly volume velocity | 10,000 h$^{-1}$ |
| ratio H$_2$/2 CO + 3 CO$_2$ | 1.2 |

The catalytic performances of these catalysts are reported hereinafter in table 2. The activity is expressed in terms of production, in kilogram (kg) of product per kg of catalyst and per hour.

The selectivity to methanol, expressed in carbon atoms percent with respect to all the carbon oxides, is always ranging from 99 to 100%.

Table I summarizes the main characteristics of the various steps of catalysts manufacture.

The composition of the catalysts is given in table 2 and the proportions are given in % by weight of metal with respect to the total metals weight in the catalyst. The performances are given after 100 hours of run and after 1,000 hours of run. Ln designates a metal from the group of rare earths and/or zirconium, M designates a metal from the group consisting of silver, palladium, platinum and rhenium.

EXAMPLE 18

One liter of catalyst A, as pellets of 2 mm height and 2.4 mm diameter, is tested in methanol synthesis reaction, in liquid phase, in a reactor of 4 cm diameter and 3 meters height.

The reduction of the catalyst is performed in gaseous phase, at atmospheric pressure, in successive stages, between 190° C. and 240° C., by means of a hydrogen-nitrogen mixture consisting of nitrogen containing 1% hydrogen.

After reduction of the catalyst, 270 liters per hour of solvent (C$_{12}$-C$_{18}$ paraffin cut) are introduced simultaneously with synthesis gas under a pressure of 75 bars. Gas and liquid flow downwardly. The operating conditions are as follows:

| Pressure | 75 bars |
|---|---|
| Temperature | 250° C. |
| Ratio H$_2$/2 CO + 3 CO$_2$ | 1 |
| Hourly volume velocity | 15,800 h$^{-1}$ |

In these conditions 0.54 kg of methanol are produced per kg of catalyst and per hour. This production remains over more than 2,000 hours of run.

EXAMPLE 19

Catalyst B, described in example 5, has been also tested for methanol decomposition. The catalyst was previously reduced by a mixture of hydrogen and nitrogen of about 5.5% hydrogen content, in successive temperatures stages within the range of 140-260° C., under atmospheric pressure. The reaction itself takes place at 290° C. under a pressure of 30 bars, with a liquid hourly volume velocity of 3 h$^{-1}$. The methanol conversion to a mixture containing CO, CO$_2$ and H$_2$ is about 95% after 100 hours and 94.5% after 1,000 hours of run.

TABLE 1

| Example | Catalyst | Step a Residence time | Step a pH | Step a Obtained precipitate homogeneity | Step a Obtained precipitate diagram | Step b Sodium content % by weight | Step d Granulometry (mm) | Step f pH | Step f Na Content % by weight | Step h T °C. | Step h Time |
|---|---|---|---|---|---|---|---|---|---|---|---|
| 1 | A | 10 mn | 6.8-7.2 | homogeneous | flat | 0.17% | 0.1 mm | 4.5 | 0.020% | 120° C. | 5 s |
| 2 | A$_1$ | 11 mn | 6.8-7.2 | homogeneous | flat | 0.18% | 0.1 mm | 4.2 | 0.019% | 40° C. then 120° | 16 h 3 h |
| 3 | A$_2$ | 10 mn | 6.8-7.2 | homogeneous | flat | 0.17% | 0.1 mm | 8.5 | 0.150% | 120° C. | 5 s |
| 4 | A$_3$ | 10 mn | 7.0-7.3 | homogeneous | flat | 0.224% | 0.1 mm | Not done | 0.224% | 120° C. | 5 s |
| 5 | B | 11 mn | 6.5-7.0 | homogeneous | flat | 0.15% | 0.2 mm | 4.5 | 0.032%[b] | 110° C. | 8 s |
| 6 | B$_1$ | 11 mn | 6.5-7.0 | homogeneous | flat | 0.15% | 0.2 mm | 4.5[b] | 0.010% | 110° C. | 8 s |
| 7 | C | 10 mn | 6.8-7.2 | homogeneous | flat | 0.17% | 0.1 mm | 4.5 | 0.030% | 120° C. | 5 s |
| 8 | D | 12 mn | 6.4-7.0 | homogeneous | flat | 0.16% | 0.2 mm | 4.5 | 0.020% | 110° C. | 8 s |
| 9 | E$_1$ | 15 mn | 6.6-7.1 | homogeneous | flat | 0.18% | 0.1 mm | 4.5 | 0.020% | 140° C. | 5 s |
| 10 | E | 15 mn | 6.6-7.1 | homogeneous | flat | 0.18% | 0.1 mm | 4.5 | 0.020% | 140° C. | 5 s |
| 11 | F | 20 mn | 6.5-7.0 | homogeneous | flat | 0.17% | 0.1 mm | 4.5 | 0.0196% | 120° C. | 5 s |
| 12 | G | 10 mn | 6.8-7.2 | homogeneous | flat | 0.20% | 0.1 mm | 4.5 | 0.034% | 110° C. | 8 s |
| 13 | H | 20 mn | 6.8-7.2 | homogeneous | flat | 0.17% | 0.15 mm | 4.5 | 0.0256% | 120° C. | 5 s |
| 14 | I | 10 mn | 6.8-7.2 | homogeneous | flat | 0.20% | 0.1 mm | 4.5 | 0.032% | 120° C. | 5 s |
| 15 | K | 12 mn | 6.8-7.2 | homogeneous | flat | 0.17% | 2 mm | 4.5 | 0.07% | 120° C. | 5 s |
| 16 | L | 10 mn | 6.8-7.2 | homogeneous | flat | 0.18% | 0.1 mm | 4.5 | 0.02% | 120° C. | 60 s |
| 17 | M | 45 mn | 6.8-7.2 | — | show[a] lines | 0.18% | 0.1 mm | 4.5 | 0.02% | 120° C. | 5 s |

[a]The diagram shows the existence of a partially crystallized product.
[b]Washed twice at pH = 4.5

TABLE 2

| Example | Catal. | Formula | Na % | Cu % | Al % | Zn % | Ln % | M % |
|---|---|---|---|---|---|---|---|---|
| 1 | A | Cu$_1$Al$_{0,4}$Zn$_{0,3}$Na$_{0,817 \times 10-3}$O$_{1,9}$ | 0,020 | 67,64 | 11,48 | 20,86 | — | — |
| 2 | A$_1$ | Cu$_1$Al$_{0,4}$Zn$_{0,3}$Na$_{0,776 \times 10-3}$O$_{1,9}$ | 0,0190 | 67,64 | 11,48 | 20,86 | — | — |
| 3 | A$_2$ | Cu$_1$Al$_{0,4}$Zn$_{0,3}$Na$_{0,61 \times 10-2}$O$_{1,9}$ | 0,150 | 67,53 | 11,46 | 20,84 | — | — |
| 4 | A$_3$ | Cu$_1$Al$_{0,4}$Zn$_{0,3}$Na$_{0,91 \times 102}$O$_{1,9}$ | 0,224 | 67,48 | 11,46 | 20,83 | — | — |
| 5 | B | Cu$_1$Al$_{0,3}$La$_{0,15}$Zn$_{0,45}$Na$_{0,17 \times 10-2}$O$_{2,275}$ | 0,032 | 52,12 | 6,64 | 24,13 | 17,08 | — |
| 6 | B$_1$ | Cu$_1$Al$_{0,3}$La$_{0,15}$Zn$_{0,45}$Na$_{0,53 \times 10-3}$O$_{2,275}$ | 0,010 | 52,12 | 6,64 | 24,13 | 17,08 | — |
| 7 | C | Cu$_1$Al$_{0,4}$Ce$_{0,05}$Zn$_{0,35}$Na$_{0,168 \times 10-2}$O$_{2,05}$ | 0,030 | 60,95 | 10,35 | 21,94 | 6,72 | — |
| 8 | D | Cu$_1$Al$_{0,45}$Zn$_{0,35}$Pd$_{0,007}$Na$_{0,863 \times 10-3}$O$_{2,035}$ | 0,020 | 63,97 | 12,22 | 23,03 | — | 0,75 |
| 9 | E$_1$ | Cu$_1$Al$_{0,45}$Zn$_{0,35}$Pd$_{0,007}$Na$_{0,863 \times 10-3}$O$_{2,035}$ | 0,020 | 63,97 | 12,22 | 23,03 | — | 0,75 |

TABLE 2-continued

| | | | | | | | |
|---|---|---|---|---|---|---|---|
| 10 | E | $Cu_1Al_{0,45}Zn_{0,35}Pd_{0,007}Na_{0,863} \times 10-3O_{2,035}$ | 0,020 | 63,97 | 12,22 | 23,03 | — | 0,75 |
| 11 | F | $Cu_{0,8}Ag_{0,025}Al_{0,35}Zn_{0,5}Na_{0,815} \times 10-3O_{1,84}$ | 0,0196 | 53,13 | 9,86 | 34,16 | — | 2,82 |
| 12 | G | $Cu_1Al_{0,45}Zn_{0,35}Re_{0,004}Na_{0,14} \times 10-2O_{2,03}$ | 0,034 | 63,98 | 12,22 | 23,03 | — | 0,749 |
| 13 | H | $Cu_1Al_{0,3}La_{0,1}Zn_{0,45}Pd_{0,01}Na_{0,13} \times 10-2O_{2,28}$ | 0,0256 | 54,76 | 6,97 | 25,35 | 11,97 | 0,92 |
| 14 | I | $Cu_1Al_{0,2}Pr_{0,1}Zn_{0,55}Na_{0,165} \times 10-2O_{2,03}$ | 0,032 | 53,39 | 4,53 | 30,21 | 11,84 | — |
| 15 | K | $Cu_1Al_{0,4}Zn_{0,3}Na_{0,287} \times 10-2O_{1,9}$ | 0,070 | 67,59 | 11,48 | 20,86 | — | — |
| 16 | L | $Cu_1Al_{0,4}Zn_{0,3}Na_{0,817} \times 10-3O_{1,9}$ | 0,020 | 67,64 | 11,48 | 20,86 | — | — |
| 17 | M | $Cu_1Al_{0,4}Zn_{0,3}Na_{0,817} \times 10-3O_{1,9}$ | 0,020 | 67,64 | 11,48 | 20,86 | — | — |
| 18 | A | $Cu_1Al_{0,4}Zn_{0,3}Na_{0,817} \times 10-3O_{1,9}$ | 0,020 | 67,64 | 11,48 | 20,86 | — | — |

| | | | Performance after 100 h | | | Performance after 1000 h | | |
|---|---|---|---|---|---|---|---|---|
| Example | Catal. | Formula | T °C. | P bars | Produc. | T °C. | P bars | Produc. |
| 1 | A | $Cu_1Al_{0,4}Zn_{0,3}Na_{0,817} \times 10-3O_{1,9}$ | 240 | 60 | 0,70 | 245 | 60 | 0,70 |
| 2 | $A_1$ | $Cu_1Al_{0,4}Zn_{0,3}Na_{0,776} \times 10-3O_{1,9}$ | 270 | 60 | 0,50 | 280 | 60 | 0,45 |
| 3 | $A_2$ | $Cu_1Al_{0,4}Zn_{0,3}Na_{0,61} \times 10-2O_{1,9}$ | 270 | 60 | 0,40 | 275 | 60 | 0,35 |
| 4 | $A_3$ | $Cu_1Al_{0,4}Zn_{0,3}Na_{0,91} \times 10-2O_{1,9}$ | 270 | 60 | 0,35 | 280 | 60 | 0,25 |
| 5 | B | $Cu_1Al_{0,3}La_{0,15}Zn_{0,45}Na_{0,17} \times 10-2O_{2,275}$ | 230 | 60 | 0,68 | 235 | 60 | 0,66 |
| 6 | $B_1$ | $Cu_1Al_{0,3}La_{0,15}Zn_{0,45}Na_{0,53} \times 10-3O_{2,275}$ | 220 | 60 | 0,70 | 225 | 60 | 0,68 |
| 7 | C | $Cu_1Al_{0,4}Ce_{0,05}Zn_{0,35}Na_{0,168} \times 10-2O_{2,05}$ | 230 | 60 | 0,70 | 235 | 60 | 0,67 |
| 8 | D | $Cu_1Al_{0,45}Zn_{0,35}Pd_{0,007}Na_{0,863} \times 10-3O_{2,035}$ | 220 | 60 | 0,72 | 225 | 60 | 0,70 |
| 9 | $E_1$ | $Cu_1Al_{0,45}Zn_{0,35}Pd_{0,007}Na_{0,863} \times 10-3O_{2,035}$ | 260 | 60 | 0,40 | 270 | 60 | 0,35 |
| 10 | E | $Cu_1Al_{0,45}Zn_{0,35}Pd_{0,007}Na_{0,863} \times 10-3O_{2,035}$ | 225 | 60 | 0,70 | 230 | 60 | 0,68 |
| 11 | F | $Cu_{0,8}Ag_{0,025}Al_{0,35}Zn_{0,5}Na_{0,815} \times 10-3O_{1,84}$ | 225 | 60 | 0,70 | 225 | 60 | 0,68 |
| 12 | G | $Cu_1Al_{0,45}Zn_{0,35}Re_{0,004}Na_{0,14} \times 10-2O_{2,03}$ | 230 | 60 | 0,68 | 240 | 60 | 0,64 |
| 13 | H | $Cu_1Al_{0,3}La_{0,1}Zn_{0,45}Pd_{0,01}Na_{0,13} \times 10-2O_{2,28}$ | 225 | 60 | 0,74 | 230 | 60 | 0.72 |
| 14 | I | $Cu_1Al_{0,2}Pr_{0,1}Zn_{0,55}Na_{0,165} \times 10-2O_{2,03}$ | 235 | 60 | 0,70 | 240 | 60 | 0,66 |
| 15 | K | $Cu_1Al_{0,4}Zn_{0,3}Na_{0,287} \times 10-2O_{1,9}$ | 260 | 60 | 0,4 | 265 | 60 | 0,35 |
| 16 | L | $Cu_1Al_{0,4}Zn_{0,3}Na_{0,817} \times 10-3O_{1,9}$ | 270 | 60 | 0,66 | 270 | 60 | 0,66 |
| 17 | M | $Cu_1Al_{0,4}Zn_{0,3}Na_{0,817} \times 10-3O_{1,9}$ | 245 | 60 | 0,70 | 245 | 60 | 0,50 |
| 18 | A | $Cu_1Al_{0,4}Zn_{0,3}Na_{0,817} \times 10-3O_{1,9}$ | 250 | 75 | 0,54 | 275 | 75 | 0,50 |

What is claimed as this invention is:

1. A process for manufacturing a catalyst precursor of essentially homogeneous composition, containing at least copper, zinc and aluminum as essential elements, characterized by the following steps of:

(a) contacting a solution of at least one alkali metal compound selected from the group consisiting of bicarbonates, carbonates and hydroxides with an essentially homogeneous solution containing, as salts and/or soluble complexes, at least copper, zinc and aluminum metals, said contacting step being performed at a pH of about 6.3–7.3, so as to form an amorphous homogeneous precipitate, having a flat diagram in X-ray diffraction, of at least copper, zinc and aluminum metals, the residence time of said precipitate in the mother liquors being from 0.1 to 30 minutes, (b) washing with water the precipitate obtained in step (a) until its content by weight of alkali metals is reduced to about 0.1–0.3% weight of the metals present, (c) drying and then roasting the washed precipitate obtained in step (b) so as to convert it to a mixture of oxides, (d) crushing said mixture of oxides to particles of a size smaller than about 0.5 mm, when the particle size of the mixture of oxides from step (c) is greater than 0.5 mm, (e) forming an aqueous suspension of the mixture of oxides of particle size smaller than about 0.5 mm, (f) washing the suspension of oxides obtained in step (e) by means of an aqueous solution of acid, said solution having a pH lower than about 6.7, so as to reduce its alkali metals content to less than about 0.05% by weight of the metals present, (g) separating the mixture of dealkalinized oxides obtained in step (f) from the washing waters.

2. A process for manufacturing a catalyst according to claim 1, characterized by the following steps of:

(a) contacting a solution of at, least one alkali metal selected from the group of bi-carbonates, carbonates and hydroxides, containing about 0.4–1.2 gram atoms per liter of alkali metals cations, with an essentially homogeneous solution containing as soluble salts and/or complexes, at least copper, zinc and aluminum metals, at a total concentration of about 0.2–0.6 gram-atoms per liter, said contacting step being performed at a pH of about 6.3–7.3 and at a temperature of about 20°–80° C., so as to form an amorphous homogeneous precipitate, having a flat diagram in X-ray diffraction, of at least copper, zinc and aluminum metals, the residence time of said precipitate in the mother-liquors being 0.1–30 minutes, (b) washing the resultant precipitate so as to reduce its alkali metals content to a value of about 0.05–0.2% by weight of the metals present, (c) drying and then roasting the precipitate obtained in step (b) so as to convert it to a mixture of oxides, said roasting step being performed at a temperature of about 250°–500° C., (d) crushing said mixture of oxides to particles of a size smaller than about 0.5 mm when the mixture of oxides obtained from step (c) is of higher granulometry, (e) forming an aqueous suspension containing about 0.5–10% by weight of oxides from the oxides mixture of particle size smaller than about 0.5 mm, (f) washing the oxides of the suspension obtained from step (e) by means of an aqueous solution of acid, said solution having a pH lower than about 6, at a temperature of about 15°–45° C., so as to reduce the content of alkali metals to value lower than about 0.05% by weight of the metals present, (g) separating the dealkalinized oxides mixture obtained in step (f), from the washing waters, (h) spray-drying the dealkalinized oxides mixture obtained in step (g) at a temperature of about 60°–150° C., with a residence time of about 1–10 seconds, so as to obtain a product having an oxides content of about 60–80% by weight, (i) thermally activating the essentially homogeneous dry oxides mixture obtained in step (h), at a temperature of about 250°–500° C.

3. A process for manufacturing a catalyst precursor according to claim 1, characterized in that the residence time of the precipitate in the mother liquors in step (a) is shorter than about 12 minutes.

4. A process according to claim 1, characterized in that the oxides mixture in suspension during step (e) has a particle size smaller than about 0.05 mm and the formed oxides suspension contains about 1.5-6% by weight of oxides.

5. A process according to claim 1, characterized in that, during step (f), the washing of the oxides suspension is performed by means of a diluted solution of nitric acid having a pH of about 2-5, until the content of alkali metals be reduced to about 0.005-0.035% by weight with respect to the oxides.

6. A process according to claim 1, characterized in that one or more additional metals selected from the group formed of rare earths, zirconium, silvered, palladium and rhenium, are introduced into the catalyst precursor during the step (a).

7. A process according to claim 1 characterized in that one or more additional metals, selected from the group formed of palladium, platinum, rhenium and silver, are introduced by impregnating the oxides mixture obtained in step (i) with a solution of salts and/or complexes of these metals, free of sulfur and halogen in their compositions, the catalyst precursor being then spray-dried at a temperature of about 60°–150° C.

8. A catalyst precursor obtained according to the process of claim 1, characterized in that it contains at least one additional metal selected from the group formed of rare earths, zirconium, palladium, rhenium and silver, the proportions by weight of each metal with respect to the total weight of the metals present being:

| | | |
|---|---|---|
| Zirconium | = | 2–18% |
| Rare earths | = | 2–18% |
| Palladium | = | 0.01–0.9% |
| Rhenium | = | 0.01–0.9% |
| Silver | = | 0.5–5% |

9. A catalyst obtained according to the process of claim 2, whose homogeneity is such that the variations of the atomic ratios Cu/Al and Cu/Zn are smaller than about 15% with respect to the average value of said ratios at the scale of 50 Angströms (5 nm); the specific surface of the catalyst being about 50–150 $m^2.g^{-1}$.

10. A process according to claim 1, wherein at least one additional metal, consisting essentially of a rare earth, zirconium, passadium platinum, rhenium, silver or at least one alkali metal is introduced into the catalyst precursor in step (a).

11. A process according to claim 10, wherein the dealkalinized oxide product of step (g) is spray-dried.

12. A process according to claim 11, wherein the spray-dried product has an oxides content of about 60–80% by weight.

13. A process according to claim 11, wherein the spray-drying is performed at a temperature of about 60°–150° C. and for 1–10 seconds.

14. A process according to claim 10, wherein the amounts of metal salts or complexes used for the formation of the catalyst precursor in step (a) are such that the proportions by weight of each metal element with respect to the total weight of the metals present in the catalyst precursor are:

| | | |
|---|---|---|
| Copper | | 25–80% |
| Zinc | | 10–50% |
| Aluminum | | 4–25%. |
| Rare earths and/or zirconium | = | 0–20% |
| Palladium | = | 0–1% |
| Platinum | = | 0–1% |
| Rhenium | = | 0–1% |
| Silver | = | 0–5% |
| Alkali metals | = | 0–0.05%. |

15. A catalyst precursor produced according to the process of claim 1.

16. A catalyst precursor produced according to the process of claim 12.

17. A catalyst precursor obtained according to the process of claim 1, consisting essentially of copper, zinc, aluminum and at least one alkali metal, the proportions be weight of each metal with respect to the total weight of the metals present being:

| | |
|---|---|
| Copper | 25–80% |
| Zinc | 10–50% |
| Aluminum | 4–25% |
| Alkali metals | 0.005–0.035%. |

18. A catalyst precursor obtained according to the process of claim 1 consisting essentially of copper, zinc, aluminum, at least one alkali metal and at least one additional metal selected from the group consisting essentially of the rare earth metals, zirconium, palladium, platinum, rhenium and silver, the proportions by weight of each metal with respect to the total weight of the metals present being:

| | |
|---|---|
| Copper | 25–80% |
| Zinc | 10–50% |
| Aluminum | 4–25% |
| Alkali metals | 0.005–0.035% | and, when present,

| | |
|---|---|
| Rare earth metals | 2–18% |
| Zirconium | 2–18% |
| Palladium | 0.01–0.9% |
| Platinum | 0.01–0.9% |
| Rhenium | 0.01–0.9% |
| Silver | 0.5–5%. |

19. A catalyst precursor according to claim 16, consisting essentially of copper, zinc, aluminum and at least one alkali metal whose homogeneity is such that the variation of the atomic ratios Cu/Al and Cu/Zn are smaller than about 15% with respect to the average value of said ratios at the scale of 50 angstroms (5nm).

20. A catalyst precursor according to claim 17, consisting essentially of copper, zinc, aluminum, at least one alkali metal and at least one additional metal selected from the group consisting of rare earth metals, zirconium, palladium, platinum, rhenium and silver, whose homogeneity is such that the variation of the atomic ratios Cu/Al and Cu/Zn are smaller than about 15% with respect to the average value of the ratios at the scale of 50 Angstroms (5nm).

21. A catalyst according to claim 9, wherein the variations of the atomic ratios are smaller than about 10% with respect to the average value of said ratios.

22. A catalyst produced according to the process of claim 2.

* * * * *

UNITED STATES PATENT AND TRADEMARK OFFICE
CERTIFICATE OF CORRECTION

PATENT NO. : 4,596,782

DATED : June 24, 1986

INVENTOR(S) : PHILIPPE COURTY ET AL

It is certified that error appears in the above-identified patent and that said Letters Patent is hereby corrected as shown below:

Column 17, line 53: reads "earth, zirconium, passadium platinum, rhenium, silver"

should read -- earth, zirconium, palladium, platinum, rhenium, silver --

Signed and Sealed this

Thirtieth Day of September 1986

[SEAL]

Attest:

DONALD J. QUIGG

Attesting Officer     Commissioner of Patents and Trademarks